(12) United States Patent
Bowers, III et al.

(10) Patent No.: US 10,509,015 B2
(45) Date of Patent: Dec. 17, 2019

(54) DETECTING FAULTY COLLECTION OF VIBRATION DATA

(71) Applicant: Computational Systems, Inc., Knoxville, TN (US)

(72) Inventors: Stewart V. Bowers, III, Knoxville, TN (US); William A. Davis, Oak Ridge, TN (US)

(73) Assignee: Computational Systems, Inc., Knoxville, TN (US)

( * ) Notice: Subject to any disclaimer, the term of this patent is extended or adjusted under 35 U.S.C. 154(b) by 381 days.

(21) Appl. No.: 15/420,933

(22) Filed: Jan. 31, 2017

(65) Prior Publication Data

US 2018/0217109 A1    Aug. 2, 2018

(51) Int. Cl.
| | | |
|---|---|---|
| *G01N 29/44* | (2006.01) | |
| *G01H 17/00* | (2006.01) | |
| *G01N 29/46* | (2006.01) | |
| *G01N 29/14* | (2006.01) | |
| *G01N 29/40* | (2006.01) | |
| *G01N 29/04* | (2006.01) | |
| *G05B 19/04* | (2006.01) | |

(52) U.S. Cl.
CPC ......... *G01N 29/4463* (2013.01); *G01N 29/04* (2013.01); *G01N 29/40* (2013.01); *G01N 2291/023* (2013.01)

(58) Field of Classification Search
CPC .................. G01N 29/04; G01N 29/40; G01N 2291/0258; G01N 2291/015; G01N 2291/023; G01N 29/4463; G01N 29/46; G01N 29/449; G01N 29/4445; G01N 29/14; G01N 29/4427; G01N 29/44; G01N 29/4409; G01N 29/48; G01M 99/005; G01H 13/00; G01H 17/00
See application file for complete search history.

(56) References Cited

U.S. PATENT DOCUMENTS

| | | | | |
|---|---|---|---|---|
| 2002/0183644 | A1* | 12/2002 | Levendowski | A61B 5/048 600/544 |
| 2010/0128385 | A1* | 5/2010 | Hara | G11B 5/5582 360/77.04 |
| 2011/0040496 | A1* | 2/2011 | Banerjee | G01M 5/0033 702/34 |

(Continued)

*Primary Examiner* — Daniel S Larkin
*Assistant Examiner* — Anthony W Megna Fuentes
(74) *Attorney, Agent, or Firm* — Luedeka Neely Group, P.C.

(57) ABSTRACT

Vibration data indicative of the health of a machine is collected using a vibration sensor connected to a vibration data collector. After the vibration sensor has been attached to a measurement point on the machine, vibration data is collected that includes a bin of data having a begin time and an end time, and the vibration data is stored in memory of the vibration data collector. First and second average amplitudes of the bin of vibration data collected during first and second time windows in the measurement time period are determined. The slope of the vibration data is calculated based on the ratio of the amplitude difference between the first and second average amplitudes and the time difference between the first and second time windows. The vibration data is either retained in the memory or discarded based on the comparison of the slope to a threshold level.

14 Claims, 4 Drawing Sheets

(56) References Cited

U.S. PATENT DOCUMENTS

| | | | |
|---|---|---|---|
| 2015/0142457 A1* | 5/2015 | Marshall | G16H 50/50 705/2 |
| 2015/0300909 A1* | 10/2015 | Giunta | G01M 5/0025 702/56 |
| 2018/0216487 A1* | 8/2018 | Michel | F01D 17/02 |

* cited by examiner

DETECTING FAULTY COLLECTION OF VIBRATION DATA

FIELD

This invention relates to the field of machine vibration monitoring. More particularly, this invention relates to a system for detecting and discarding undesirable vibration data prior to analysis of the data.

BACKGROUND

In industrial facilities that utilize machines having rotating components, vibration generated by the machines may be monitored to detect abnormal conditions that could lead to machine failure. Machine vibration may be monitored using an on-line data collection system or using a handheld portable vibration data collector carried by a technician from one machine to another. Such vibration data collectors typically employ a vibration sensor, such as a piezoelectric sensor, that generates an electrical signal indicative of vibration levels of the machine. The machine data is often stored in memory in the data collector as the technician acquires vibration data, and is uploaded to a data analysis computer after completion. A data analyst may then use vibration data analysis software running on the data analysis computer that processes the vibration data to provide information to the analyst regarding operational performance of the machines for which data was collected.

Sometimes the vibration data collected along the route is unusable due to problems in the way the data was collected. In some instances, the problems are due to electrical transients in the sensor signal, overloading of the sensor, or exposure of the sensor to mechanical shock immediately prior to the collection of the data.

What is needed is a method for detecting that vibration data is undesirable for data analysis purposes as the data is collected, and discarding the undesirable data prior to data analysis.

SUMMARY

The above and other needs are met by a method for collecting vibration data indicative of the health of a machine using a vibration sensor that may be connected to a vibration data collector or to an on-line data collection system. A preferred embodiment of the method includes the following steps:
 (a) attaching the vibration sensor to a measurement point on the machine;
 (b) collecting vibration data that includes a data bin that extends over a measurement time period having a begin time and an end time;
 (c) storing the vibration data in memory;
 (d) determining a first average amplitude of the vibration data collected during a first time window in the measurement time period;
 (e) determining a second average amplitude of the vibration data collected during a second time window in the measurement time period;
 (f) determining the slope of the vibration data based on the ratio of the amplitude difference between the first and second average amplitudes and the time difference between the first and second time windows; and
 (g) retaining or discarding the vibration data collected in step (b) based on comparison of the slope to one or more threshold levels.

In some embodiments, step (g) includes deleting the vibration data collected in step (b) from the memory if the slope is greater than a first threshold level.

In some embodiments, steps (b) through (g) are repeated until the slope is less than the first threshold level, at which point the vibration data collected in step (b) is retained in the memory.

In some embodiments, step (g) includes:
 (g1) prompting an operator to choose to retain or discard the vibration data collected in step (b) if the slope is less than a first threshold level and greater than a second threshold level, wherein the second threshold level is less than the first threshold level; and
 (g2) retaining or discarding the vibration data collected in step (b) based on the choice of the user.

In some embodiments, the prompting of step (g1) is accomplished by a visual prompt on a display screen of the vibration data collector.

In some embodiments, the first time window begins at the begin time of the measurement time period and the second time window ends at the end time of the measurement time period.

In some embodiments, the time difference between the first and second time windows is determined to be the difference in time between the mean time of the first time window and the mean time of the second time window.

In some embodiments, the widths of the first and second time windows are no greater than one half of the bin measurement time period.

Alternative embodiments of the invention provide a method for collecting vibration data that includes the following steps:
 (a) attaching a vibration sensor to a measurement point on a machine;
 (b) collecting vibration data that includes a data bin that extends over a measurement time period having a begin time and an end time;
 (c) storing the vibration data in memory;
 (d) determining a first average amplitude of the vibration data collected during a first time window in the measurement time period;
 (e) determining a second average amplitude of the vibration data collected during a second time window in the measurement time period;
 (f) determining an amplitude difference between the first and second average amplitudes;
 (g) determining to retain or discard the vibration data collected in step (b) based on comparison of the amplitude difference to one or more threshold levels; and
 (h) if it is determined in step (g) to discard the vibration data, repeating steps (b) through (g) until it is determined in step (g) to retain the vibration data.

In some embodiments, step (g) includes deleting the vibration data collected in step (b) from the memory if the amplitude difference is greater than a first threshold level, In some embodiments, the method includes performing step (h) until the amplitude difference is less than the first threshold level, at which point the vibration data collected in step (b) is retained in the memory.

In yet another aspect, embodiments of the invention are directed to a vibration data collector for collecting vibration data indicative of the health of a machine. The vibration data collector includes a vibration sensor, an analog-to-digital converter, memory, and a processing device. The vibration sensor attaches to a measurement point on the machine and generates vibration signals based on vibration of the machine during a measurement time period having a begin time and an end time. The analog-to-digital converter converts the vibration signals to digital vibration data, and the memory stores the vibration data. The processing device operates on the vibration data based on execution of software commands that:

determine a first average amplitude of the vibration data collected during a first time window in the measurement time period;

determine a second average amplitude of the vibration data collected during a second time window in the measurement time period;

determine the slope of the vibration data based on the ratio of the amplitude difference between the first and second average amplitudes and the time difference between the first and second time windows; and retain the vibration data in the memory or delete the vibration data from the memory based on comparison of the slope to one or more threshold levels.

In some embodiments, the processing device deletes the vibration data from the memory if the slope is greater than a first threshold level.

In some embodiments, the processing device continues the collection of vibration data at the measurement point until the slope is less than the first threshold level, at which point the collected vibration data is retained in the memory.

In some embodiments, the execution of commands by the processing device:

generates a message on a display device that prompts a user of the vibration data collector to choose to retain or discard the vibration data if the slope is less than a first threshold level and greater than a second threshold level, wherein the second threshold level is less than the first threshold level; and causes the vibration data to be retained in the memory or deleted from the memory based on the choice of the user.

BRIEF DESCRIPTION OF THE DRAWINGS

Other embodiments of the invention will become apparent by reference to the detailed description in conjunction with the figures, wherein elements are not to scale so as to more clearly show the details, wherein like reference numbers indicate like elements throughout the several views, and wherein.

DETAILED DESCRIPTION

Figure 1:
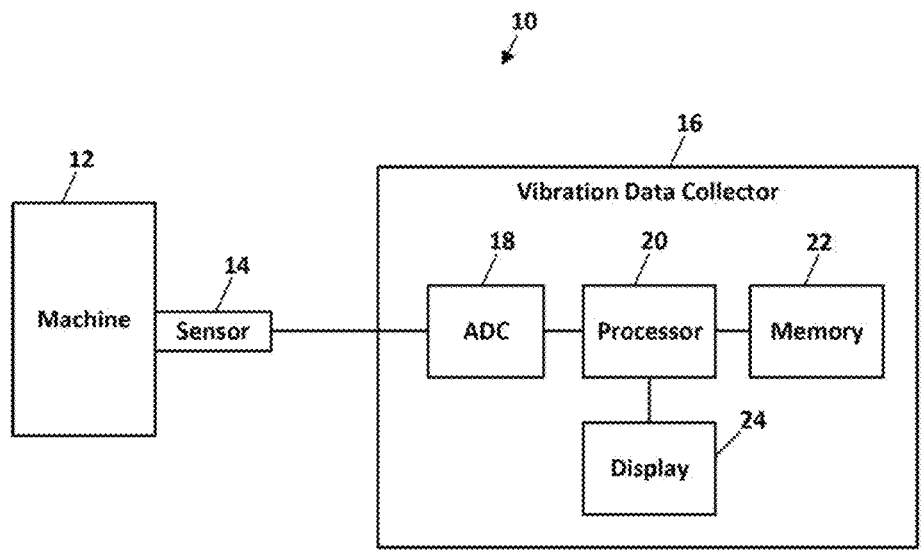
FIG. 1 depicts an apparatus for collecting machine vibration data according to an embodiment of the invention.

Embodiments described herein are directed to eliminating a noise problem referred to as "ski-slope noise" that may be observed in machine vibration data collected on a machine using a vibration data collection system, such as the exemplary system 10 depicted in FIG. 1. The system 10 includes a sensor 14 that a user attaches to a machine 12 to be tested in any measurement mode (such as an analyze mode or along a route). In a preferred embodiment, the sensor 14 is a piezoelectric sensor that generates an electrical voltage signal that is indicative of the level of vibration generated by the machine 12. The sensor 14 is electrically connected to a vibration data collector 16, such as a CSI 2140 Machinery Health Analyzer. The data collector 16 includes an analog-to-digital converter (ADC) 18 that converts the analog voltage signal from the sensor 14 into digital vibration data. A processor 20 in the data collector 16 receives the vibration data and processes it according to methods described herein, in which the data is either discarded or retained in memory 22.

Figure 2:
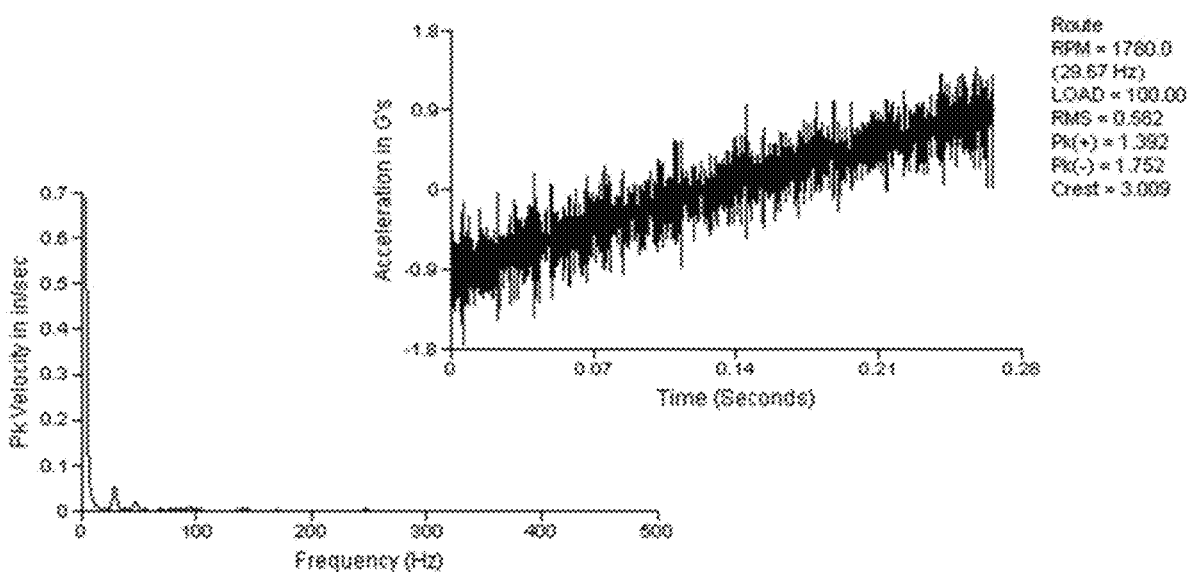
FIGS. 2 and 3 depict time domain and frequency domain plots of machine vibration data collected using the apparatus of FIG. 1.

FIG. 2 illustrates the "ski-slope noise" problem. In the lower left portion of FIG. 2 is an exemplary peak velocity frequency spectrum derived from data collected using the system 10 depicted in FIG. 1. The large spectral amplitude at very low frequency, which has a steep downward slope toward higher frequency, is referred to as a "ski-slope." In this example, the peak is not so large in amplitude that it completely overshadows all other spectra features, although it is still more than a factor of ten larger than any other spectral peak. The upper right portion of FIG. 2 depicts a time waveform of the vibration data from which the frequency spectrum is derived. One of the most striking things about the waveform is the obvious slope in acceleration amplitude over time.

There are two common events that induce the sensor 14 to generate a vibration signal having the characteristics depicted in FIG. 2. One event is an electrical transient generated in the sensor circuitry when the sensor 14 is initially connected to its power source or in the case of excessive vibration which will cause the sensor to overload. The other event is the subjection of the sensor to a large mechanical shock, such as may occur in the process of placing the sensor on the machine 12 to be monitored.

Figure 3:
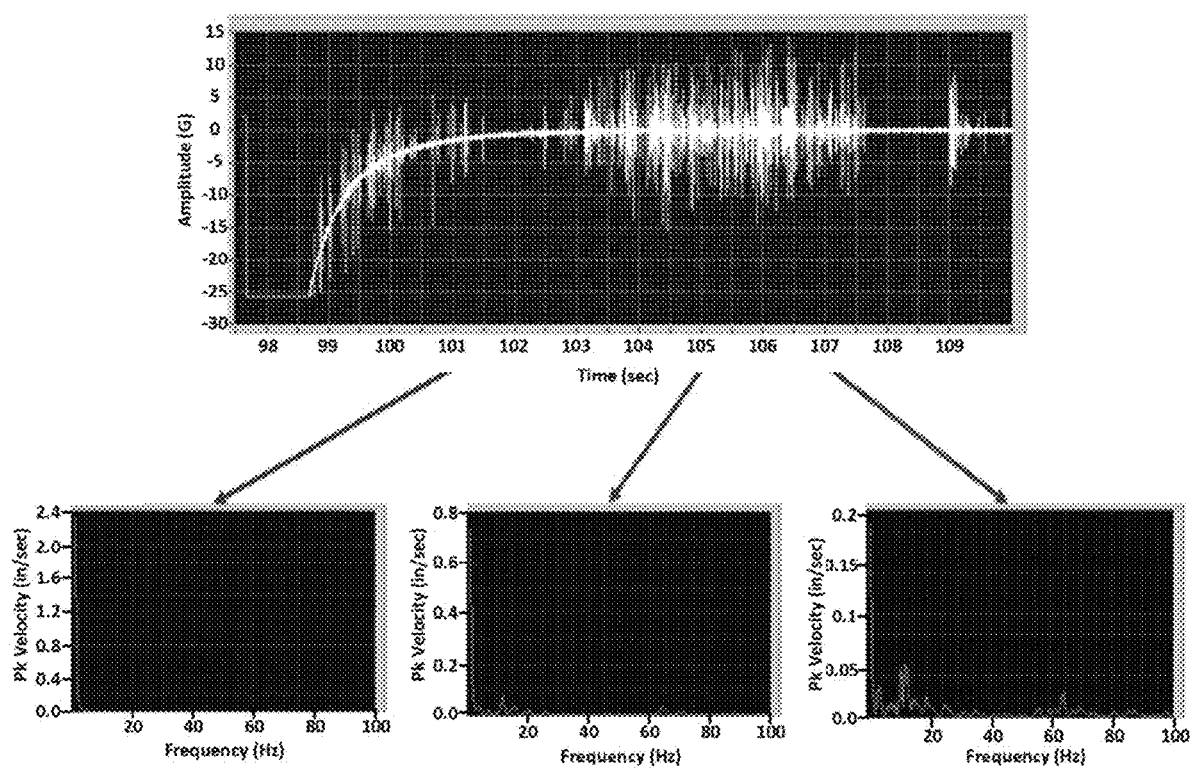

FIG. 3 depicts data collected from an accelerometer using a digital recorder, where the accelerometer had been disconnected from the recorder, thereby interrupting its electrical power, and then reconnected to the recorder. The upper image in FIG. 3 shows the raw vibration waveform signal from the sensor as digitized by the digital recorder. The upper image illustrates the recovery of the raw waveform signal. At approximately 98.7 seconds the sensor was reconnected to the data collector. The subsequent 10 to 11 seconds of data show the recovery of the vibration signal. The three lower images in FIG. 3 are spectra computed from the upper waveform beginning at 2.3 seconds, 6.3 seconds, and 8.3 seconds after the reconnection event. As the three spectra indicate, the amplitude of the ski-slope feature decreases by more than a factor of ten over this six-second time range. Although there is still a prominent ski-slope peak in the 8.3-second spectrum, the desired vibration signal is readily visible.

In embodiments described herein, the processor 20 of the vibration data collector 16 computes the slope of the vibration time waveform signal in real time. Since the computed slope correlates to the amplitude of the ski-slope feature in the frequency spectrum, the computed slope is an indicator of the severity of the ski-slope problem. Because the slope can be computed in real time, data that exhibits a severe ski-slope problem can be discarded in real time to avoid using memory space to store undesirable data.

Figure 4:
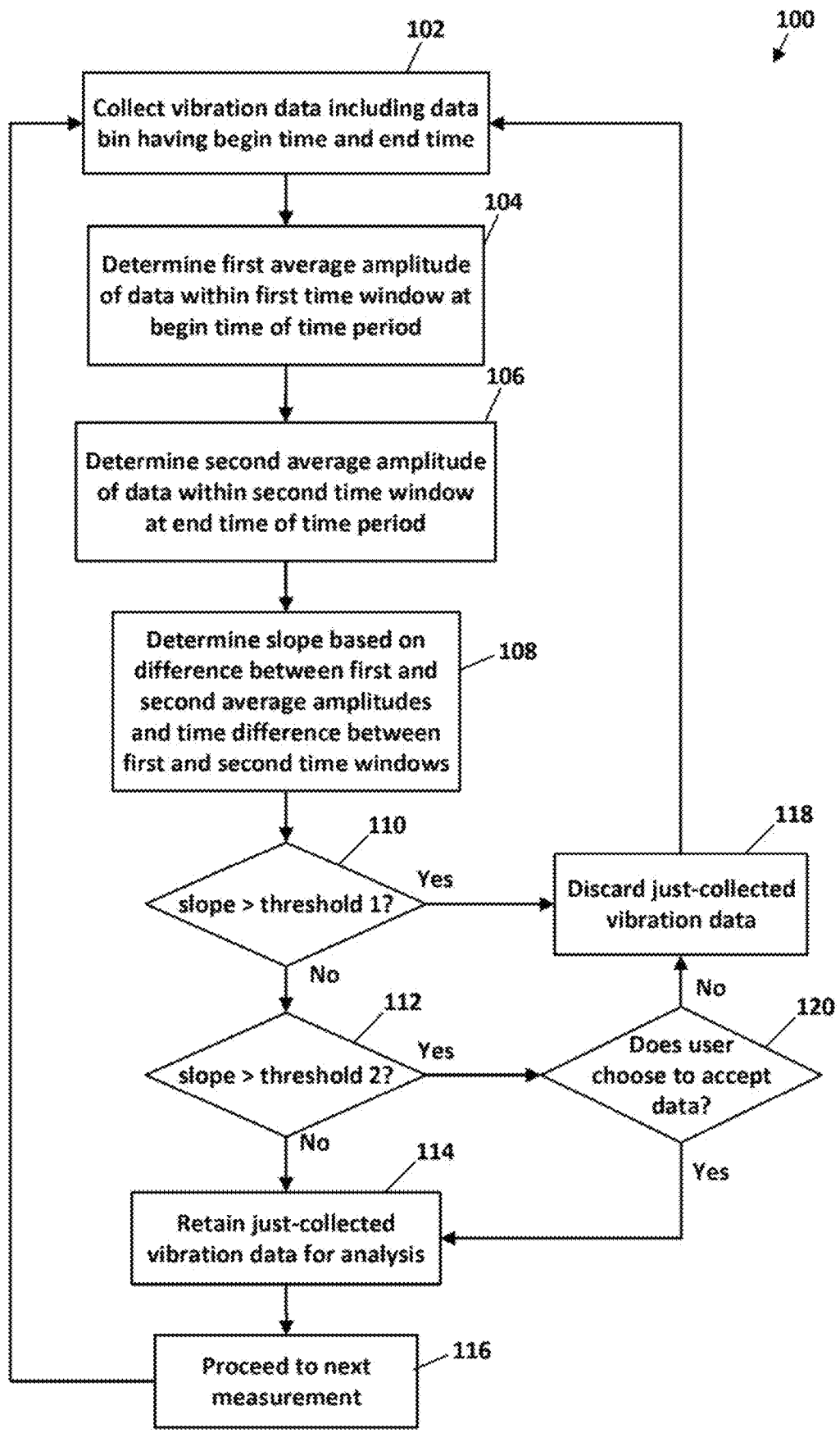
FIG. 4 depicts a method for processing machine vibration data to detect and discard undesirable data.
Figure 5A:
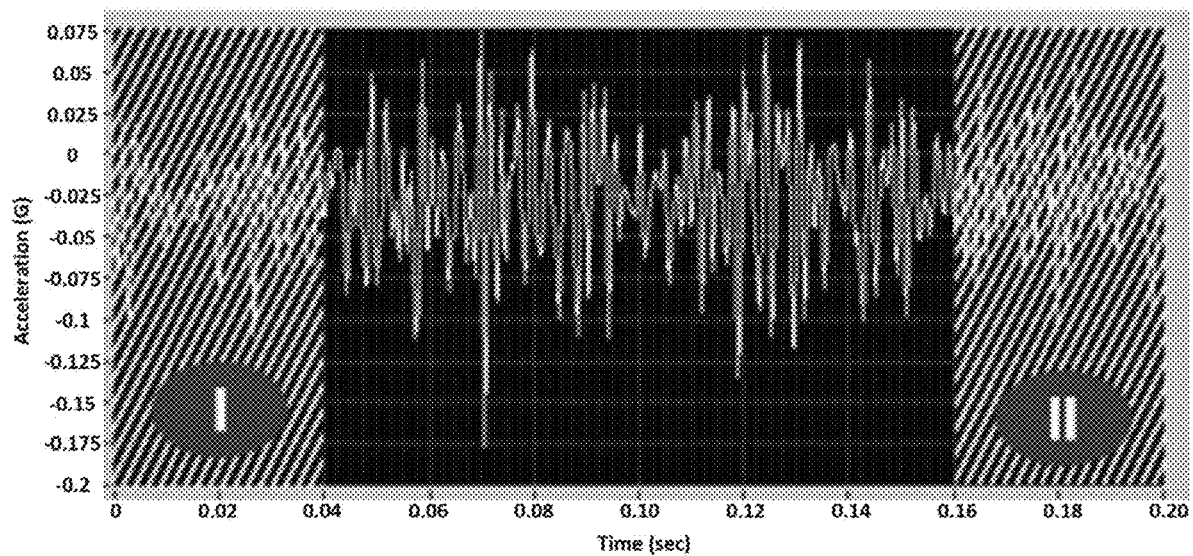
FIGS. 5A and 5B depict time domain plots of machine vibration data processed according to the method of FIG. 4.

FIG. 4 depicts an exemplary method 100 executed by the processor 20 to detect and discard undesirable vibration data collected with a vibration data collector. To begin a first measurement, the user attaches the sensor 14 to a measurement location on the machine 12 and uses the data collector 16 to collect a bin of vibration data over some time period (step 102). As the term is used herein, a bin of vibration data is a subset of the total waveform data needed for the particular vibration measurement. An exemplary bin of vibration data spanning a 0.2 second time period is depicted in FIG. 5A. It should be appreciated that the invention is not limited to any particular length of time for the initial data collection. In the example of FIG. 5A, a time period of 0.2 seconds is long enough to contain at least 6 cycles of the machine running speed for a machine driven by a two-pole AC motor. This exemplary time period is also typically short enough that it can be sampled and computations completed in a shorter time than required to do a full vibration data collection for any particular measurement.

In a preferred embodiment, the processor 20 calculates the mean amplitude of the measured vibration signal within a first time window near the start of the data collection time period (step 104). This first time window within the bin is indicated by the cross-hatched section I in FIG. 5A, which may be as wide as one-half the total width of the data bin collection time period. In the current example, the width of the first time window is 0.04 seconds. The processor 20 also calculates the mean amplitude of the measured vibration signal within a second time window near the end of the data bin collection time period (step 106). This second time window is indicated by the cross-hatched section II in FIG. 5A, which may be as wide as one-half the total width of the data bin collection time period. In the current example, the width of the second time window is also 0.04 seconds. In a preferred embodiment, the amplitudes of all data points of the waveform within each time window are averaged to determine a single mean amplitude value for each window.

Figure 5B:
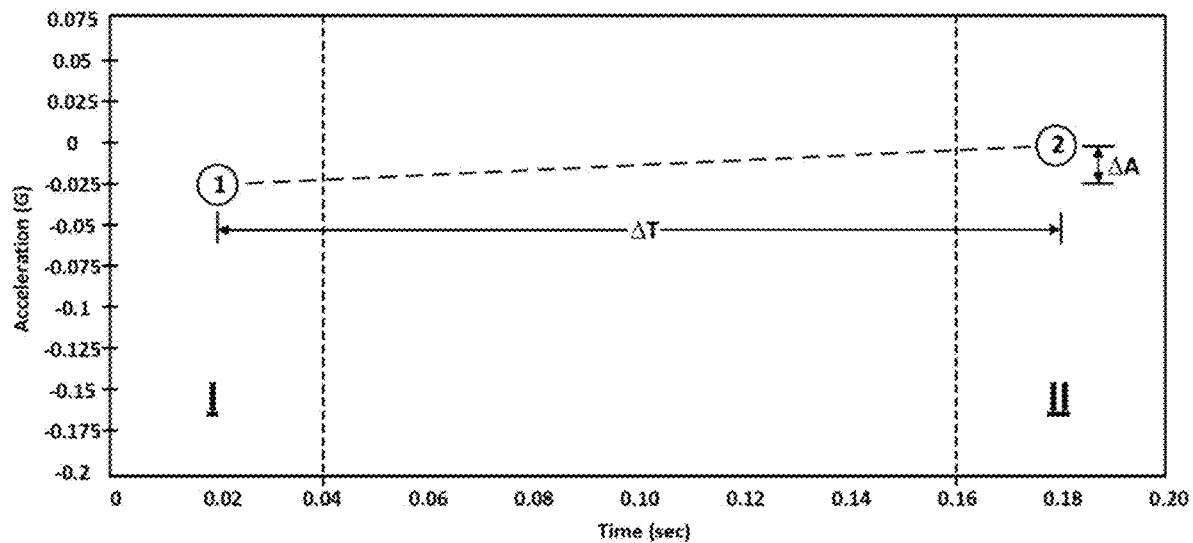

The mean amplitude value for the first time window is represented by circle 1 in FIG. 5B. The mean amplitude value for the second time window is represented by circle 2 in FIG. 5B. The difference in amplitude between the two mean amplitude values is represented as ΔA and the mean time difference between the first and second time windows is represented as ΔT in FIG. 5B. The processor 20 calculates a simple slope S according to:

$$S = \Delta A \div \Delta T \text{ (step 108)}.$$

In the example of FIGS. 5A-5B, ΔA=0.025 g and ΔT=0.16 sec. and $$S = 0.025 \div 0.16 = 0.15625 \text{ g/sec}.$$

The slope S is then compared to a stored first threshold value (step 110). If the slope S is greater than the first threshold value, the data collected at step 102 is discarded by deleting it from the memory 22 (step 118). If the slope S is not greater than the first predetermined threshold value, the slope S is compared to a stored second threshold value that is less than the first threshold value (step 112). If the slope S is not greater than the second threshold value, the data of the total waveform is retained in memory after acquisition is completed in association with an identification of the current measurement point (step 114). If the slope S is greater than the second threshold value, a message is displayed on the display device 24 of the data collector 16 prompting the user to either accept the data as good enough or reject the data as undesirable (step 120). If the user accepts the data, the data is retained in memory in association with the identification of the current measurement route point (step 114). If the user chooses to reject the data, the data collected at step 102 is discarded by deleting it from the memory 22 (step 118).

The user proceeds to the next data collection point (step 116), and process steps are repeated until acceptable data has been collected at all desired measurement points. Data that remains in the memory 22 after step 114 will be available for consideration by a data analyst after completion of the route.

In an alternative embodiment, only the difference in amplitude ΔA between the two mean amplitude values is considered. This embodiment does not consider the time difference ΔT or the slope S. The algorithm proceeds as described above, except it uses a threshold for the average amplitude difference ΔA instead of the slope S. For good data, ΔA should be very close to zero.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method for collecting vibration data indicative of health of a machine, the method comprising:
    (a) attaching a vibration sensor to a measurement point on the machine;
    (b) collecting vibration data including a bin of vibration data that extends over a measurement time period having a begin time and an end time;
    (c) storing the vibration data in memory;
    (d) determining a first average amplitude of a first portion of the bin of vibration data collected during a first time window that includes the begin time of the measurement time period;
    (e) determining a second average amplitude of a second portion of the bin of vibration data collected during a second time window that includes the end time of the measurement time period;
    (f) determining a slope of the vibration data based on a ratio of an amplitude difference between the first and second average amplitudes and a time difference between a first time in the first time window and a second time in the second time window; and
    (g) retaining or discarding the bin of vibration data collected in step (b) based on comparison of the slope to one or more threshold levels.

2. The method of claim 1 wherein step (g) comprises deleting the vibration data collected in step (b) from the memory if the slope is greater than a first threshold level.

3. The method of claim 2 further comprising repeating steps (b) through (g) until the slope is less than the first threshold level, and retaining the vibration data collected in step (b) in memory.

4. The method of claim 1 wherein step (g) comprises:
    (g1) prompting an operator to choose to retain or discard the vibration data collected in step (b) if the slope is less than a first threshold level and greater than a second threshold level, wherein the second threshold level is less than the first threshold level; and
    (g2) retaining or discarding the vibration data collected in step (b) based on the choice of the operator.

5. The method of claim 4 wherein the prompting is accomplished with a visual prompt on a display screen.

6. The method of claim 1 wherein the first time window begins at the begin time of the measurement time period and the second time window ends at the end time of the measurement time period.

7. The method of claim 1 wherein the first time in the first time window is a mean time of the first time window and the second time in the second time window is a mean time of the second time window.

8. The method of claim 1 wherein a width of the first time window is no greater than one half of the measurement time period, and a width of the second time window is no greater than one half of the measurement time period.

9. The method of claim 1 wherein step (c) comprises storing the vibration data in memory of a vibration data collector or memory of an on-line vibration data collection system.

10. A vibration data collector for collecting vibration data indicative of health of a machine, comprising:
 a vibration sensor operable to be attached to a measurement point on the machine and generate a bin of vibration data based on vibration of the machine at the measurement point during a measurement time period having a begin time and an end time;
 an analog-to-digital converter for converting the vibration signals to digital vibration data;
 memory for storing the vibration data;
 a processing device for operating on the vibration data based on execution of commands that:
  determine a first average amplitude of a first portion of the bin of vibration data collected during a first time window that includes the begin time of the measurement time period;
  determine a second average amplitude of a second portion of the bin of vibration data collected during a second time window that includes the end time of the measurement time period;
  determine a slope of the vibration data based on a ratio of an amplitude difference between the first and second average amplitudes and a time difference between a mean time of the first time window and a mean time of the second time window; and
  retain the vibration data in the memory or delete the vibration data from the memory based on comparison of the slope to one or more threshold levels.

11. The vibration data collector of claim 10 wherein the analog-to-digital converter, the memory and the processing device are components of a portable handheld measurement device or of an on-line measurement system.

12. The vibration data collector of claim 10 wherein execution of commands by the processing device causes deletion of the vibration data from the memory if the slope is greater than a first threshold level.

13. The vibration data collector claim 12 wherein execution of commands by the processing device causes collection of vibration data to continue at the measurement point until the slope is less than the first threshold level, at which point the collected vibration data is retained in the memory.

14. The vibration data collector of claim 10 wherein execution of commands by the processing device:
 generates a message on a display screen that prompts a user of the vibration data collector to choose to retain or discard the vibration data if the slope is less than a first threshold level and greater than a second threshold level, wherein the second threshold level is less than the first threshold level; and
 causes the vibration data to be retained in the memory or deleted from the memory based on the choice of the user.

* * * * *